United States Patent [19]

Cartilier et al.

[11] Patent Number: 5,616,343

[45] Date of Patent: Apr. 1, 1997

[54] CROSS-LINKED AMYLOSE AS A BINDER/DISINTEGRANT IN TABLETS

[75] Inventors: Louis Cartilier, Beaconsfield; Mircea A. Mateescu, Verdun; Yves Dumoulin, Ste-Julie, all of Canada; Vincent Lenaerts, Paris, France

[73] Assignee: Labopharm, Inc., Quebec, Canada

[21] Appl. No.: 37,119

[22] Filed: Mar. 25, 1993

[51] Int. Cl.$^6$ .................................................. A61K 9/20
[52] U.S. Cl. ........................ 424/464; 424/493; 424/488; 424/479; 424/461
[58] Field of Search ........................ 424/479, 461, 424/464, 465, 488, 474

[56] References Cited

U.S. PATENT DOCUMENTS

| | | | |
|---|---|---|---|
| 2,987,445 | 6/1961 | Levesque | 167/82 |
| 3,087,860 | 4/1963 | Endicott | 167/82 |
| 3,622,677 | 11/1971 | Short et al. | 424/361 |
| 4,072,535 | 2/1978 | Short et al. | 106/210 |
| 4,088,798 | 5/1978 | Michaelis | 427/3 |
| 4,230,687 | 10/1980 | Sair et al. | 424/22 |
| 4,344,968 | 8/1982 | Aoda et al. | 424/365 |
| 4,369,308 | 1/1983 | Trubiano | 536/106 |
| 4,713,249 | 12/1987 | Schroder | 424/488 |
| 4,755,397 | 7/1988 | Eden et al. | 427/213.3 |
| 4,761,289 | 8/1988 | Shalati et al. | 424/468 |
| 4,812,445 | 3/1989 | Eden et al. | 514/60 |
| 4,814,182 | 3/1989 | Graham et al. | 424/484 |
| 4,933,185 | 6/1990 | Wheatley et al. | 424/461 |
| 4,952,402 | 8/1990 | Sparks et al. | 424/419 |
| 5,108,758 | 4/1992 | Allwood et al. | 424/468 |

FOREIGN PATENT DOCUMENTS

| | | |
|---|---|---|
| 2041774 | 5/1992 | Canada . |
| 0499648 | 1/1991 | European Pat. Off. . |

OTHER PUBLICATIONS

Remington's Pharmaceutical Sciences 18th edition p. 1326.
Brook et al., J. Pharm. Sci., 1968, 57, 481–484.
Mateescu et al., Analytical Letters, 1985, 18, 79–91.
Bolhuis, Pharm. Weekblad, 1973, 108, 469–481.
Lerk et al., Pharm. ACTA Helv. 52, Nr. 3 (1977), 33–39.
Analytical Letters, 14(B17 & 18), 1501–1514 (1981).
Journal of Polymer Science: Polymer Physics Edition, vol. 21, 983–997 (1983).
Pharm. ACTA Helv. 55, Nr. 6 (1980).
Pharm. ACTA Helv. 55, Nr. 7–8 (1980).
Pharm. ACTA Helv. 56, Nr 4–5 (1981).

*Primary Examiner*—Thurman K. Page
*Assistant Examiner*—William E. Benston, Jr.
*Attorney, Agent, or Firm*—Foley & Lardner

[57] ABSTRACT

The present invention is concerned with the manufacture of solid dosage units (pharmaceutical and others). More specifically, the invention is related to powders of cross-linked amylose, having a specific cross-linking degree for use as tablet binders and disintegrants.

20 Claims, 7 Drawing Sheets

CROSS-LINKED AMYLOSE AS A BINDER/DISINTEGRANT IN TABLETS

FIELD OF THE INVENTION

The present invention is related to powders of cross-linked amylose, having a specific cross-linking degree for use as a tablet binder and/or disintegrant, the tablets being prepared by direct compression.

BACKGROUND OF THE INVENTION

In the pharmaceutical industry, tablets appear to be the most advantageous form for the administration of a drug. Packaging and handling are normal operations onto which pharmaceutical products are submitted, which makes tablets the preferred choice. Additionally, tablets are frequently employed in non pharmaceutical fields such as fish foods, plant growth regulators, pesticides, herbicides and the like.

These tablets must show good mechanical qualities in view of the manufacturing process involved and the subsequent handling and packaging. The most important mechanical properties are the hardness and the resistance to friability. These features are closely related to one another since an increase in tablet hardness generally leads to a decrease in tablet friability. The term hardness describes the resistance of the tablet to stresses and strains of transportation and storage. Usually, one measures the crushing-strength defined as "that compressional force which, when applied diametrically to a tablet, just fractures it" (Brook et al. *J. Pharm. Sci.*, 1968, 57, 481–484). If the hardness of the tablet is insufficient i.e. when the crushing-strength value is too low, tablets are likely to break, especially during handling when they are subjected to repeated shocks. Furthermore, excessive friability may cause dusting and crumbling of the tablet, resulting in a diminution in active ingredient dosage and in a poor appearance of the tablet.

Thus, the manufacture of tablets involves the optimization of these two characteristics. If a quick release of the drug is desired, then the tablet must also possess acceptable disintegration characteristics both in vivo and in vitro.

The simplest and most economical procedure for the manufacturing of tablets is the direct compression of all the ingredients distributed homogeneously. The procedure i.e. the powder compression in a tablet puncher follows directly the dry blending of one or more active ingredients and at least one of the following: filler, binder, disintegrant and lubricant, and the like.

Materials such as sodium chloride, saccharose, salicylamide, hexamethylenetetramine and the like are readily directly compressed alone in dry form into a coherent and compact mass in a conventional tablet puncher. However, the majority of active ingredients require a binding agent to maintain the drug particles together in a tablet. Such binding agent increases the strength of the compressed tablet and decreases its friability, leading to an improvement in the tablet appearance and mechanical characteristics. An appropriate binding agent possesses flowing properties, can be blended easily and is inert and non-toxic. Conventional binders currently in use include: microcrystalline cellulose (Avicel PH-101™ and PH-102™) polyvinylpyrrolidone (Kollidon™, Plasdone™), cornstarch, wheat starch, potato starch, modified starches, gums, and the like. All these products are usually employed in direct compression at a minimum concentration level of 20%.

Disintegration rate is important when the tablet is contacted with fluids such as body fluids. Tablets should immediately fall apart into distinct particles whenever the drug is to be released very quickly. They must disintegrate rapidly enough to provide adequate blood levels of drug.

If quick disintegration of the tablet is required, disintegrants are added. A effective disintegrated is an agent that promotes destruction of the tablet physical integrity. Typical disintegrants are: corn starch, gelatinized starches (Sta Rx™), modified starches e.g. sodium starch glycolate (Primojel™).

Co-pending application U.S. Ser. No. 787,721 filed Oct. 31, 1991 discloses cross-linked amylose having a cross-linking degree of 1 to 10, which possesses controlled release properties when mixed with a pharmaceutical product. However, such controlled release properties are observed only if the amount of cross-linked amylose is above 40% by weight in the tablet.

Short et al. (U.S. Pat. No. 3,622,677) discloses a binder/disintegrant constituted of modified and/or cross-linked starch. However, the binding properties of their materials are considerably low, which means that a significant amount of the binder needs to be present in the tablet.

Trubiano (U.S. Pat. No. 4,369,308) describes modified starches for use as disintegrant. These starches however have poor binding properties.

Some materials, for example microcrystalline cellulose (Avicel PH 101™ and Avicel PH 102™) present binding and disintegrating characteristics of both binders and disintegrants. Despite the existence of many binders and disintegrants, pharmaceutical researchers have continued their efforts to develop improved materials capable of being employed as a binder and/or as a disintegrant in the preparation of tablets by direct compression.

SUMMARY OF THE INVENTION

In accordance with the present invention, there is now provided an improved binder for the manufacture of tablets. The binder of the present invention also acts as a disintegrant. More specifically, the binder of the present invention consists in cross-linked amylose having a cross-linking degree of from 6 to 30. The binder can be used in the manufacture of tablets by conventional techniques such as direct compression.

Tablets comprising the above binder also fall within the scope of the present invention, and may be chewable tablets. The concentration of cross-linked amylose in the tablet must be lower than 35% by weight.

DETAILED DESCRIPTION OF THE INVENTION

The cross-linking of amylose is well known in the literature. For example, it can be carried out by reacting amylose with epichlorohydrin in an alkaline medium. Several cross-linking agents are available to cross-link amylose, such as 2,3-dibromopropanol, epichlorohydrin, epichlorohydrin being more preferred. Most preferred cross-linked amylose include those obtained by cross-linking 6 to 30 g of epichlorohydrin per 100 g of amylose, corresponding to a cross-linking degree of 6 to 30.

Surprisingly, it has been discovered that the above cross-linked amylose can be dry mixed in an amount not exceeding 35% by weight with active ingredients and optionally conventional tablet excipients, such as fillers, lubricants, and the like, to prepare formulations which are directly compressible into tablets in conventional tablet punchers.

To illustrate the present invention, tablets containing cross-linked amylose of various cross-linking degrees, α-monohydrate lactose 100 mesh and magnesium stearate were prepared. The crushing strength, the friability and the disintegration times of the tablets were investigated. The results showed excellent binding and disintegrating properties for cross-linked amylose having a cross-linking degree from 6 to 30. The influence of the compressional force, the cross-linking degree and the concentration of cross-linked amylose were also carefully examined.

CROSS-LINKED AMYLOSE

Amylose is a natural substance obtained from starch, a binary compound constituted by amylose non-ramified polyglucose chain wherein the repetitive glucose units are linked by α-1,4-glucosidic bonds, and by the amylopectin branched polyglucose polymer, which contains many branching points based on α-1,6-glucosidic bonds.

The cross-linking of amylose is well-known in the literature. For example, the desired cross-linking can be carried out in the manner described by Mateescu et al. in *Analytical Letters*, 1985, 18, 79–91, by reacting amylose with epichlorohydrin in an alkaline medium.

Essentially, the amylose is swollen in an alkaline medium such as sodium hydroxide at 55° C. After complete homogenization, an appropriate amount of cross-linking agent is added and homogenization continues for 45 min. The duration of heating can be varied as well as the amount of cross-linking agent used in the reaction. The cross-linked amylose gel is then neutralized with acetic acid, washed with water/acetone and dried with pure acetone. Finally, the polymer powder is exposed to air for 3 hours and stored in hermetic glass bottles.

The binding properties of these cross-linked amylose are comparable or even superior in some instances, to microcrystalline cellulose (Avicell PH-102™) which is widely used in the field. Certain cross-linked amylose advantageously present also excellent disintegration properties, thus preventing the need of an additional excipient having these properties in the tablet.

It should be noted that the unexpected and highly effective binding properties of cross-linked amylose have not been observed with cross-linked starch or cross-linked amylopectin. This phenomenon is essentially due to the fact that amylose is constituted of linear non-ramified chains of polyglucose susceptible to be associated by hydrogen bonds. On the other hand, the presence of branched chains in amylopectin does not allow molecular rearrangements, responsible for the binding properties. Since starch contains over 75% by weight of amylopectin, it is normal that it is not as effective as amylose. Thus, the use of cross-linked amylose constitutes definitively an improvement when compared to starch.

PREPARATION OF TABLETS

The binding properties of cross-linked amylose and disintegrating properties of tablets containing same were studied. The tablets also contained α-monohydrate lactose 100 mesh as the filler and magnesium stearate as the lubricant. These latter two products are used on a current basis in the pharmaceutical industry. Furthermore, it is well-known that α-monohydrate lactose presents poor binding and disintegrating properties (Bolhuis, *Pharm. Weekblad*, 1973, 108, 469–481). Magnesium stearate is also recognized to decrease crushing-strength of lactose tablets and to increase disintegration times by hindering the water penetration into the tablet (Lerk et al., *Pharm. Acta Helv.*, 1977, 52(3), 33–39). The poor binding and disintegrating properties of the lubricant and filler used further illustrate the unexpected binding and disintegrating properties of cross-linked amylose having a cross-linking degree of 6 to 30.

Typically, α-monohydrate lactose 100 mesh and cross-linked amylose were mixed in a Turbula shaking mixer for 3 minutes. Magnesium stearate was subsequently incorporated, and the mixture further agitated for an additional 2 minutes.

Tablets weighing about 400 mg each were obtained by direct compression in a hydraulic press at 2, 4, 6 and 8 tons/cm². The tablets were of 1.26 cm diameter and thickness of about 2.0 to about 2.2 mm.

DETERMINATION OF THE TABLET CRUSHING-STRENGTH

The crushing-strength (Lerk, 1977) has been determined by using a tablet hardness tester (Strong Kobb Arner, model B124). The value is expressed in kg and is the mean of five measurements.

DETERMINATION OF THE TABLET FRIABILITY

The index of friability is determined by using a friabilitor (Pharma Test, Type PTFR II, Hainburg, Germany). 13 tablets are shaken in the apparatus for 4 min (25 rpm). The friability index is calculated according to the following equation:

$$I = (1 - M_b/M_a) \times 100$$

wherein $M_a$ = weight of the tablet before shaking;

$M_b$ = weight of the tablet after the shaking.

DETERMINATION OF THE TABLET DISINTEGRATION TIME

Disintegration times were determined according to method <701> for uncoated tablets of USP XX using 1 liter of water at 37° C. as the medium. The disintegration time reported is the mean of three measurements.

The following examples are provided to illustrate the invention rather than limit its scope. Other variations within the scope of the present invention will be easily appreciated by the skilled workman.

EXAMPLE 1

Cross-linked amylose synthesis (CLA-6): 1 kg of corn amylose (Sigma Chemicals, St. Louis) and 6 L of sodium hydroxide 1N (55° C.) are mixed in a Hobart A200-T planetary mixer. After 15 minutes of homogenization, a volume of 50.8 ml (60 g, d=1.18 g/ml) of epichlorohydrin is added slowly and homogenization continues for another 45 min. The CLA gel is then neutralized with acetic acid and washed three times through a Büchner funnel with a solution of water:acetone 60:40. The last step consists of washing and drying the resulting solid gel with pure acetone directly on a Büchner filter. Finally, the polymer is exposed to air for 3 hours and stored in hermetic glass bottles. The granulometric fraction between 50 and 250 microns was selected in all the experiments.

This polymer will be referred to as CLA-6.

Other CLA polymers are obtained under strictly identical conditions but changing the amount of epichlorohydrin to 110, 150 and 300 g to obtain CLA-11, CLA-15 and CLA-30. In the figures, CLA-0 indicates that native amylose was treated in the same manner as above, except that no epichlorohydrin was added.

EXAMPLE 2

α-monohydrate lactose 100 mesh and cross-linked amylose prepared in Example 1 were mixed in a Turbula shaking mixer for 3 minutes; magnesium stearate was added, and the mixture further agitated for 2 minutes.

The proportions of the various ingredients in the tablets are reported in Table 1. Avicel PH-102™ was used as a comparison since it is one of the better binding/disintegrating agent presently available on the market.

TABLE 1

Concentration of each ingredient in the tablets

| Mixture (number) | Lactose (%) | Mg stearate (%) | CLA content (%) |
|---|---|---|---|
| 1 | 99.8 | 0.2 | 0.0 |
| 2 | 94.8 | 0.2 | 5.0 |
| 3 | 84.8 | 0.2 | 15.0 |
| 4 | 79.8 | 0.2 | 20.0 |
| 5 | 74.8 | 0.2 | 25.0 |

Tablets weighing about 400 mg each were obtained by direct compression in a hydraulic press at 2, 4, 6 and 8 tons/cm$^2$. The tablets were of 1.26 cm diameter and thickness of about 2.0 to about 2.2 mm.

EXAMPLE 3

The crushing-strength results are presented in FIGS. 1, 2, 3 and 4. The crushing-strength (kg) is plotted against the compressional force (t/cm$^2$) for the different CLA-n prepared in example 1. The plot of the crushing-strength versus the compression force of lactose tablets deprived of binder are also reported in FIGS. 1, 2, 3 and 4 to assess clearly the effect of the compression force and the presence of the binding agent on the crushing-strength.

Figure 1:
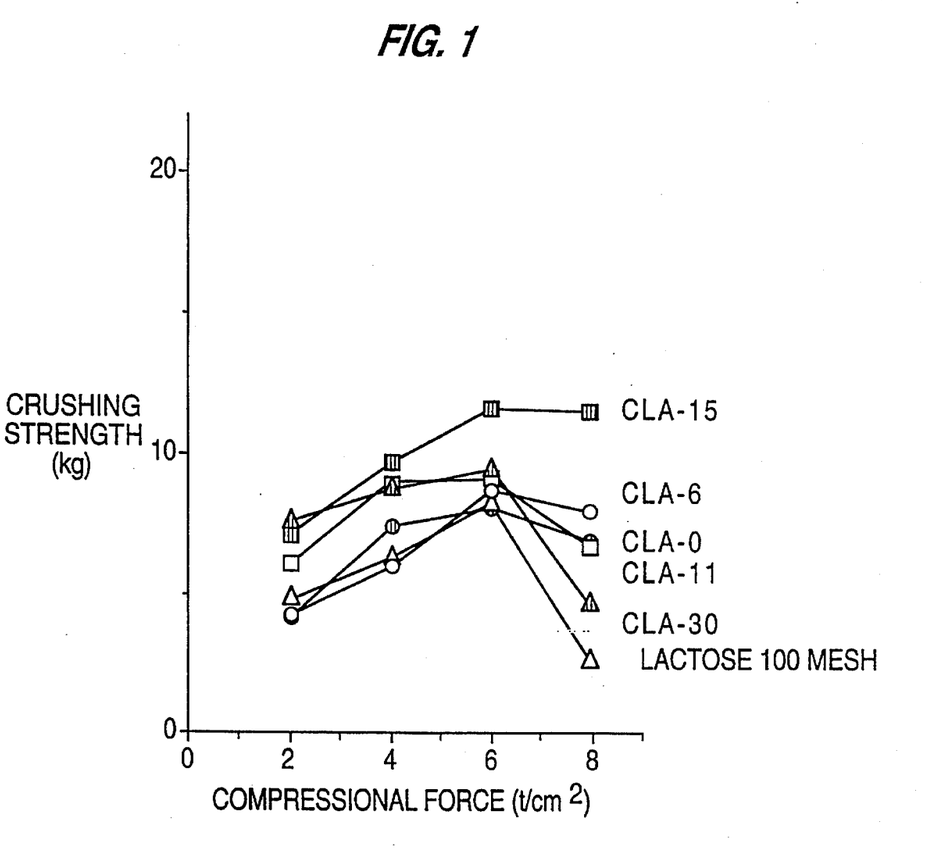
FIG. 1 illustrates hardness versus compression strength for tablets containing 5% of cross-linked amylose.
Figure 2:
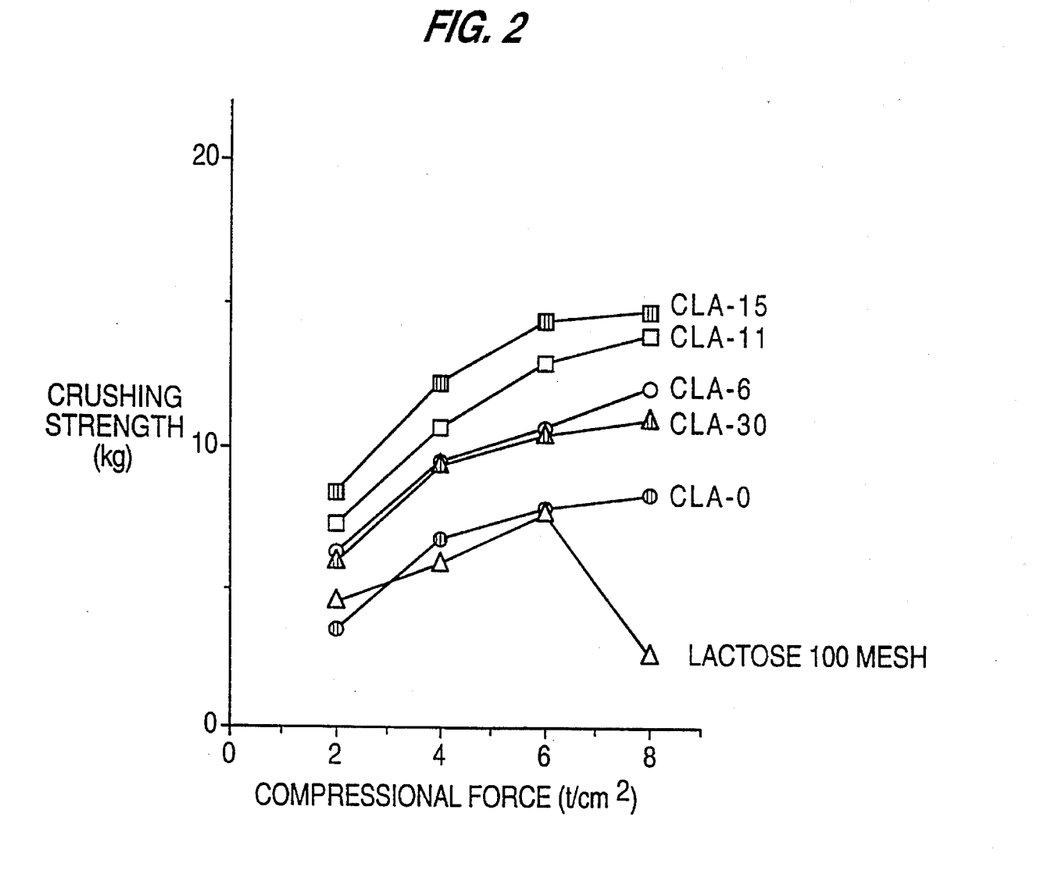
FIG. 2 illustrates hardness versus compression strength for tablets containing 15% of cross-linked amylose.
Figure 3:
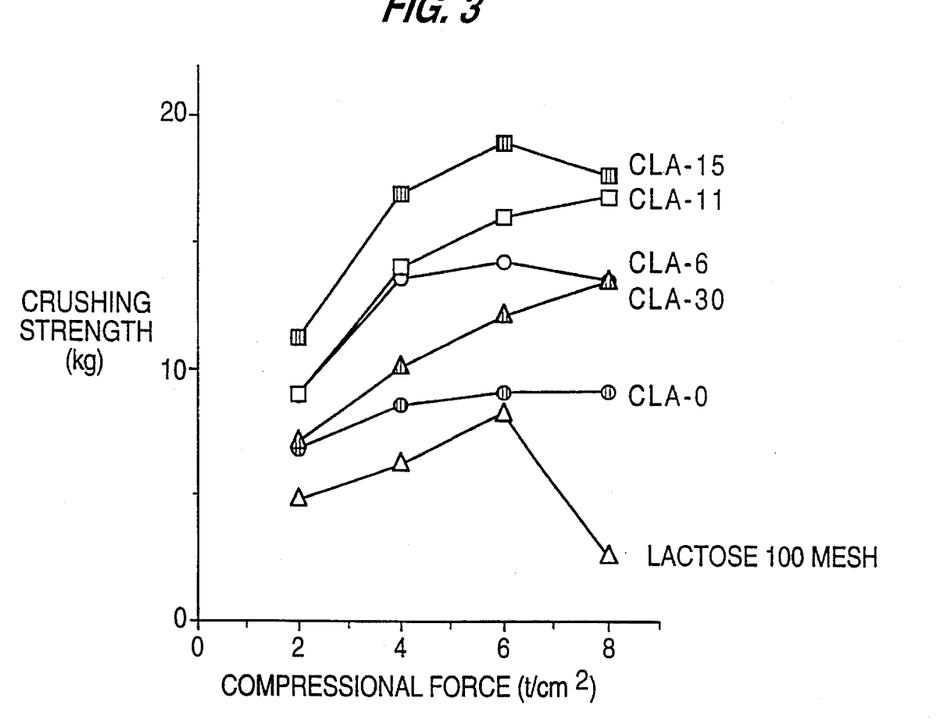
FIG. 3 illustrates hardness versus compression strength for tablets containing 20% of cross-linked amylose.
Figure 4:
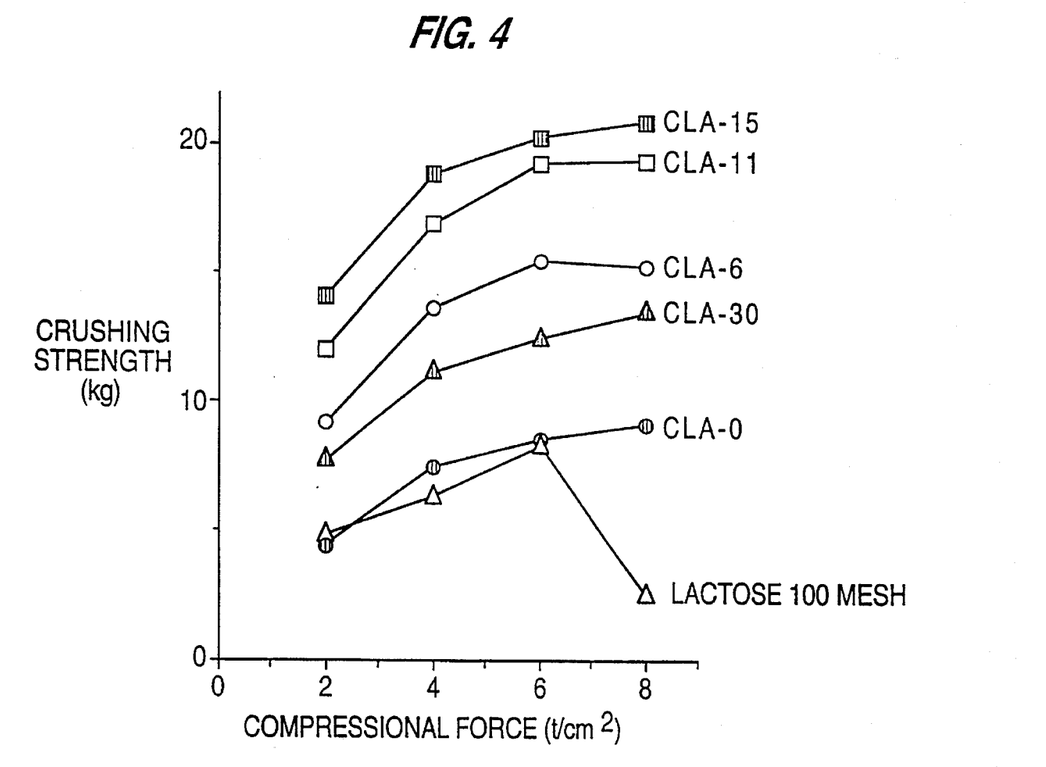
FIG. 4 illustrates hardness versus compression strength for tablets containing 25% of cross-linked amylose.

It can be seen in FIG. 1 that tablets made of lactose and magnesium stearate without any binder are not very hard and break easily (all the crushing-strength values are below 8.4 kg, which is the best value obtained). Furthermore, an increase in compression force to 8 tons/cm$^2$ causes a dramatic decrease in hardness (2.7 kg). This is caused by the lactose particles which tend to break down in smaller particles when high compressional forces are applied.

The effect of cross-linked amylose is clearly demonstrated in FIGS. 1 to 4 since their presence in the tablets leads generally to an increase in hardness. The beneficial effect is particularly evident when the concentration of cross-linked amylose is equal or higher than 15%. Thus, the cross-linked amylose concentration is an important parameter for obtaining satisfactory tablet hardness.

Figure 5:
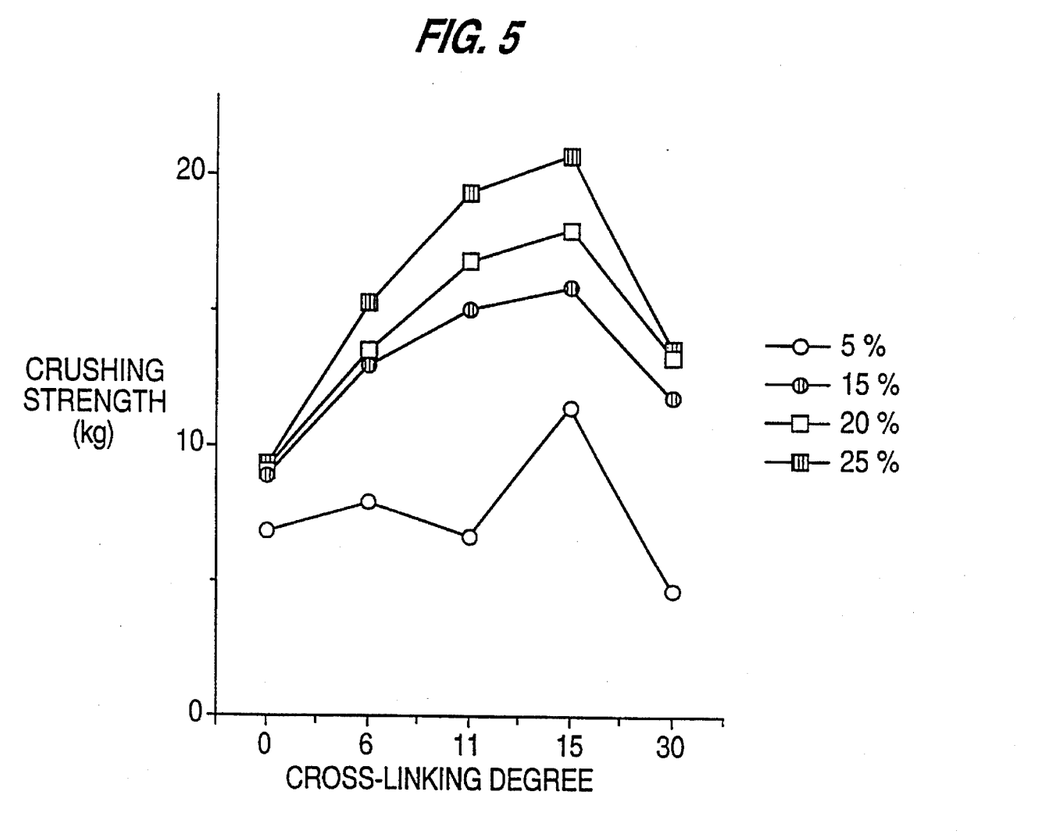
FIG. 5 illustrates the hardness versus the cross-linking degree when tablets are compressed at 8 tons/cm$^2$.

Another important point is the effect of the cross-linking degree on the tablet hardness for identical concentrations of cross-linked amylose (FIGS. 1 to 4). It can be seen that CLA-0 has almost no effect on the tablet hardness, except at a compression force of 8 tons/cm$^2$ when the polymer concentration is equal or higher than 15%. It is also apparent that the best results are obtained with a cross-linking degree of 15 (CLA-15). The crushing-strength has been plotted against the cross-linking degree for different concentrations of polymer, in the case of a compressional force equal to 8 tons/cm$^2$ to show more clearly the effect of cross-linking degree on the tablet hardness (FIG. 5). In any event, cross-linked amylose having a cross-linking degree ranging from about 6 to about 30 improved the hardness of the tablet when compared to those containing lactose and magnesium stearate and deprived of binder. Thus, the cross-linking degree of cross-linked amylose is a critical parameter in the obtention of an adequate tablet hardness.

Figure 6:
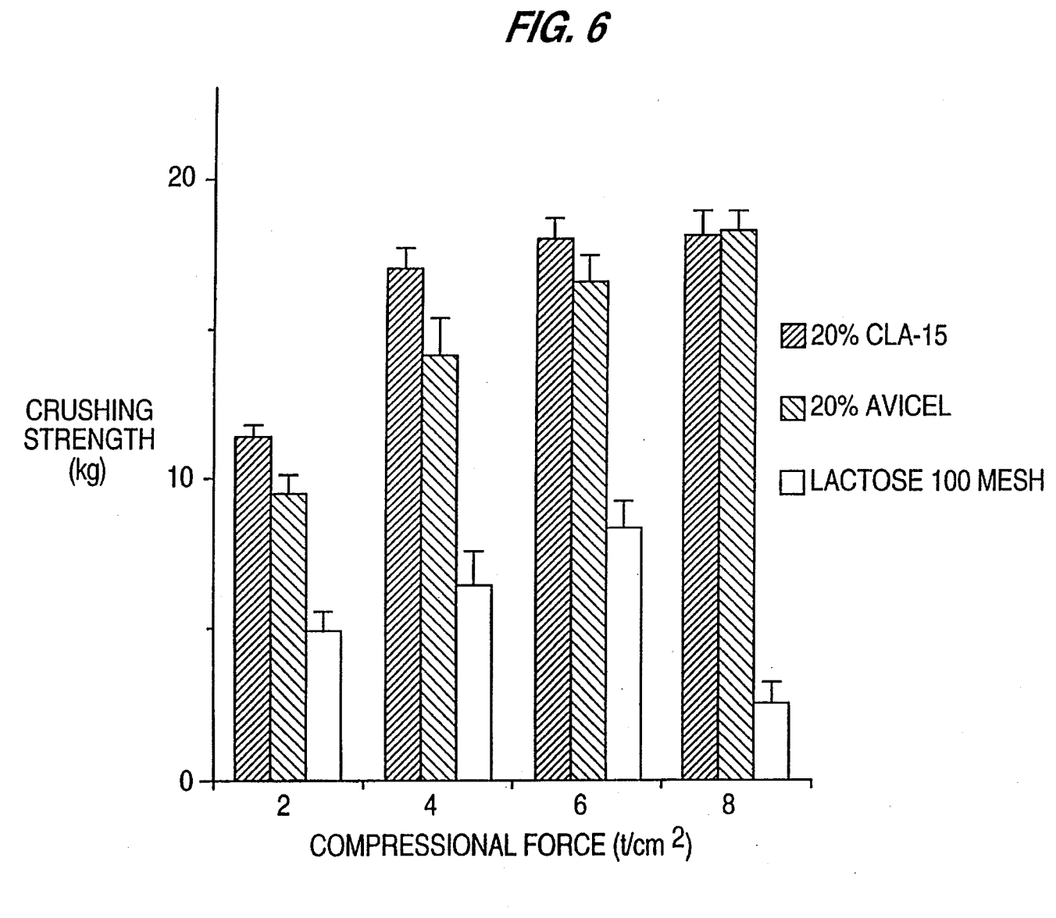
FIG. 6 illustrates the hardness versus the compression strength for tablets containing 20% by weight of Avicel or CLA-15 as the binder.
Figure 7:
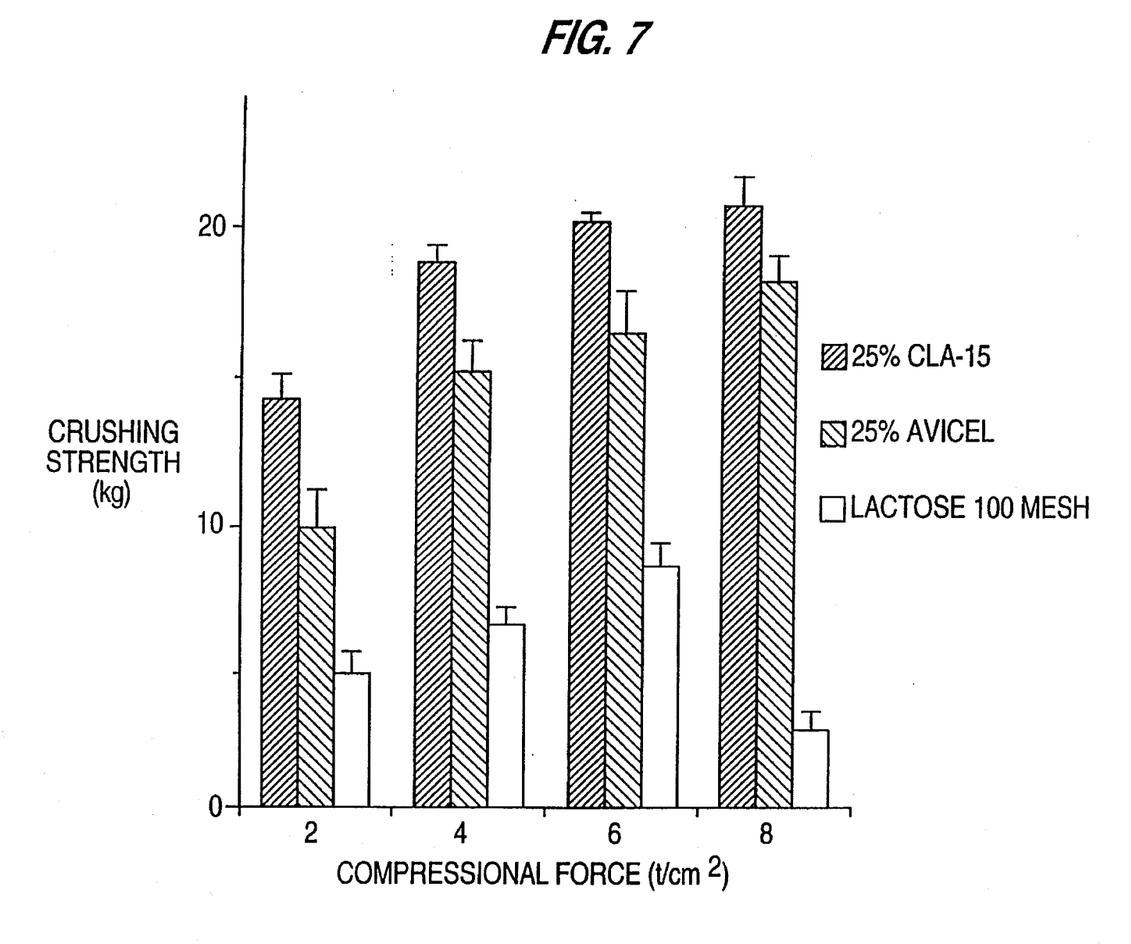
FIG. 7 illustrates the hardness versus the compression strength for tablets containing 25% by weight of Avicel or CLA-15 as the binder.

Finally, tablets containing CLA-15 were compared to tablets containing Avicel PH-102™ and tablets deprived of binder (FIGS. 6 and 7). There is clearly an improvement in the binding properties when 20% or 25% of binder are used (Avicel PH-102™ or CLA-15). Furthermore CLA-15 presented much better binding properties than Avicel PH-102™, demonstrating the utility of cross-linked amylose in the preparation of tablets by direct compression.

EXAMPLE 4

Friability results are presented in Table 2. Clearly, cross-linked amylose shows excellent binding properties leading to very low values of friability. It is particularly evident that CLA-15 again demonstrated superior binding properties when compared to other CLAs and Avicel PH-102™. The influence of the cross-linked amylose concentration is also evident, a higher binder concentration leading to a lower friability of the tablet. These results are in perfect agreement with the results obtained for hardness experiments (see Example 3).

TABLE 2

Friability of tablets

| | Compression force (tons/cm$^2$) | | | |
|---|---|---|---|---|
| | 2 | 4 | 6 | 8 |
| Binder 5% | | | | |
| CLA-0 | * | 1.09 | * | * |
| CLA-6 | * | 0.72 | * | * |
| CLA-11 | 1.28 | 0.94 | 0.75 | 1.05 |
| CLA-15 | 1.31 | 0.65 | 0.6 | 0.7 |
| CLA-30 | 1.44 | 0.85 | 0.81 | * |
| Avicel PH 102 | 1.33 | 0.64 | 0.67 | * |

TABLE 2-continued

Friability of tablets

| | Compression force (tons/cm²) | | | |
| --- | --- | --- | --- | --- |
| | 2 | 4 | 6 | 8 |
| Binder 15% | | | | |
| CLA-0 | * | 1.35 | 1.18 | 1.19 |
| CLA-6 | 0.71 | 0.46 | 0.33 | 0.40 |
| CLA-11 | 0.80 | 0.48 | 0.37 | 0.37 |
| CLA-15 | 0.68 | 0.29 | 0.28 | 0.27 |
| CLA-30 | 1.03 | 0.49 | 0.55 | 0.30 |
| Avicel PH 102 | 1.78 | 0.42 | 0.33 | 0.33 |
| Binder 20% | | | | |
| CLA-0 | * | 1.27 | 1.27 | 1.19 |
| CLA-6 | 0.39 | 0.36 | 0.34 | 0.30 |
| CLA-11 | 0.63 | 0.43 | 0.34 | 0.34 |
| CLA-15 | 0.50 | 0.27 | 0.18 | 0.20 |
| CLA-30 | 0.82 | 0.41 | 0.40 | 0.34 |
| Avicel PH 102 | 0.69 | 0.34 | 0.31 | 0.29 |
| Binder 25% | | | | |
| CLA-0 | * | 1.44 | 1.25 | 1.29 |
| CLA-6 | 0.54 | 0.40 | 0.31 | 0.22 |
| CLA-11 | 0.53 | 0.28 | 0.25 | 0.23 |
| CLA-15 | 0.30 | 0.16 | 0.15 | 0.12 |
| CLA-30 | 0.62 | 0.35 | 0.30 | 0.29 |
| Avicel PH 102 | 0.57 | 0.31 | 0.23 | 0.22 |

*Tablets broke during experiment

EXAMPLE 5

Disintegration results proved to be excellent as well for cross-linked amylose CLA-15 and CLA-30 as for Avicel PH-102™ when they are used at a concentration of 20% in the tablet. All the disintegration times were between 30 and 90 seconds for compressional forces ranging from 2 to 8 tons/cm². Mixtures of various percentages of cross-linked amylose of different cross-linking degrees were studied in regard of the disintegration times and presented similar results, that is, the disintegration times varied from 30 to 90 seconds. The cross-linked amylose used for the purpose of the present invention possesses binding properties combined with disintegrating properties as long as it is employed in accordance with the restrictions specified above.

EXAMPLE 6

CLA-8 and Cross-Linked Amylopectine-8 were synthesized in the same manner as in Example 1. Tablets containing 20% of CLA-8 and 20% of cross-linked amylopectine-8 were prepared at a compressional force of 8 tons/cm², in conditions identical to those indicated in Example 2. The crushing-strength values are reported in Table 3.

TABLE 3

Crushing-strength values of CLA-8, Cross-Linked Amylopectine-8 and lactose 100 mesh.

| CLA-8 (20%) | Cross-Linked Amylopectine-8 | Lactose 100 mesh |
| --- | --- | --- |
| 14.5 | 7.5 | 2.0 |
| 13.5 | 8.0 | 3.0 |
| 15.0 | 8.5 | 3.0 |
| 13.0 | 8.5 | 2.0 |
| 13.5 | 8.5 | 3.5 |
| mean = 13.9 | mean = 8.2 | mean = 2.7 |

Table 3 clearly illustrates that CLA binding properties are largely superior to those of cross-linked amylopectine. The beneficial effect of CLA is better even with a cross-linking degree as low as 8. Starch being largely composed of amylopectine, it becomes obvious that the use of CLA constitutes an improvement when compared to starch and that the role of amylose is of major importance, probably due to its regular non branched structure, susceptible of being stabilized by hydrogen bonds.

It is evident that the skilled workman will be able to select properly the cross-linking degree and the concentration of cross-linked amylose to formulate adequately tablets to be prepared by direct compression, these tablet being hard, non friable and readily disintegrative when placed in aqueous medium.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains, and as may be applied to the essential features hereinbefore set forth, and as follows in the scope of the appended claims.

What is claimed is:

1. A tablet obtained by direct compression of a mixture consisting essentially of an active ingredient and cross-linked amylose as a binder/disintegrant, wherein the cross-linking has been carried out with from about 6 to about 30 grams of cross-linking agent per 100 grams of amylose, and wherein the cross-linked amylose is present in the tablet in an amount not exceeding 35% by weight.

2. A tablet according to claim 1, wherein the cross-linking agent is epichlorohydrin.

3. A tablet according to claim 1, wherein the active ingredient is a drug.

4. A tablet according to claim 2, which disintegrates within 90 seconds in one liter of water at 37° C.

5. A tablet according to claim 1, which is in the form of a chewable tablet.

6. A tablet according to claim 1, further comprising at least one additional excipient.

7. A tablet according to claim 6, wherein said additional excipient is selected from the group consisting of a filler and a lubricant.

8. A tablet according to claim 1, wherein the cross-linked amylose is present in the tablet in an amount ranging from 5% to 25% by weight.

9. A tablet according to claim 8, wherein:

the cross-linking agent is epichlorohydrin;

the active ingredient is a drug; and said mixture further comprises a pharmaceutically acceptable lubricant.

10. A tablet according to claim 9, wherein said mixture further comprises a pharmaceutically acceptable filler.

11. A tablet according to claim 8, wherein the cross-linked amylose is present in the tablet in an amount ranging from 15% to 25% by weight.

12. A tablet according to claim 9, wherein the cross-linked amylose is present in the tablet in an amount ranging from 15% to 25% by weight.

13. A tablet according to claim 10, wherein the cross-linked amylose is present in the tablet in an amount ranging from 15% to 25% by weight.

14. A tablet according to claim 8, wherein the cross-linked amylose has been cross-linked with about 15% grams of cross-linking agent per 100 grams of amylose.

15. A tablet according to claim 14, wherein:

the cross-linking agent is epichlorohydrin;

the active ingredient is a drug; and said mixture further comprises a pharmaceutically acceptable lubricant.

16. A tablet according to claim 15, wherein said mixture further comprises a pharmaceutically acceptable filler.

17. A tablet according to claim 11, wherein the cross-linked amylose has been cross-linked with about 15 grams of cross-linking agent per 100 grams of amylose.

18. A tablet according to claim 17, wherein:

the cross-linking agent is epichlorohydrin;

the active ingredient is a drug; and said mixture further comprises a pharmaceutically acceptable lubricant.

19. A tablet according to claim 18, wherein said mixture further comprises a pharmaceutically acceptable filler.

20. A method of binding a tablet and enhancing disintegration of said tablet comprising the step of compressing a mixture consisting essentially of an active ingredient and cross-linked amylose as a binder/disintegrant, wherein the cross-linking has been carried out with from about 6 to about 30 grams of cross-linking agent per 100 grams of amylose, and wherein the cross-linked amylose is present in the tablet in an amount not exceeding 35% by weight.

* * * * *